US012692856B2

(12) United States Patent
Jester et al.

(10) Patent No.: US 12,692,856 B2
(45) Date of Patent: Jul. 28, 2026

(54) PUMP AND CASSETTE SYSTEM FOR USE IN MICROWAVE ABLATION

(71) Applicant: Varian Medical Systems, Inc., Palo Alto, CA (US)

(72) Inventors: Steve Jester, Eden Prairie, MN (US); Paul Joseph Hattan, Minneapolis, MN (US); Tim Bachman, Saint Paul, MN (US); Matt Goulet, Palo Alto, CA (US); Logan Ernster, Palo Alto, CA (US); Charlie Weber, Palo Alto, CA (US); Jonathan Nath, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 405 days.

(21) Appl. No.: 18/477,328

(22) Filed: Sep. 28, 2023

(65) Prior Publication Data

US 2025/0109743 A1 Apr. 3, 2025

(51) Int. Cl.
A61B 18/18 (2006.01)
F04B 43/12 (2006.01)
A61B 18/00 (2006.01)

(52) U.S. Cl.
CPC .......... F04B 43/12 (2013.01); A61B 18/1815 (2013.01); A61B 2018/00023 (2013.01); A61B 2018/00577 (2013.01)

(58) Field of Classification Search
CPC . A61B 18/18; A61B 18/1815; A61B 18/1492; A61B 18/1402; A61B 2018/00023; A61B 2018/0212; A61B 2018/00577; A61B 2018/00172; A61B 2017/0023; A61F 7/12; A61F 7/0085; A61F 2007/0054; A61F 2007/126; F04B 43/12
USPC ........ 606/20–23, 25, 33, 41, 42; 607/96, 98, 607/99, 101, 104, 105, 113, 115, 116; 604/506–508, 27, 113, 93.01
See application file for complete search history.

(56) References Cited

U.S. PATENT DOCUMENTS

2004/0215183 A1 10/2004 Hoey et al.
2004/0267340 A1* 12/2004 Cioanta ................... A61F 7/123
607/113

(Continued)

FOREIGN PATENT DOCUMENTS

GB 2606777 A 11/2022

OTHER PUBLICATIONS

The European Search Report dated Feb. 12, 2025, in corresponding European Application No. 24200787.0; 5 pages.

*Primary Examiner* — Thomas A Giuliani
(74) *Attorney, Agent, or Firm* — Morgan, Lewis & Bockius LLP; Manita Rawat

(57) ABSTRACT

An apparatus for cooling an ablation probe includes a cassette receptacle configured to accept a cassette including a supply tube for supplying a coolant to the ablation probe. The apparatus also includes a pump head movably positioned proximate the cassette receptacle. The pump head is configured to move between a loading position and an operating position. The pump head includes one or more rollers configured to engage the supply tube of the cassette when the pump head is in the operating position. The apparatus also includes an actuator coupled to the pump head. The actuator is configured to move the pump head between the loading position and the operating position.

19 Claims, 12 Drawing Sheets

(56) References Cited

U.S. PATENT DOCUMENTS

| | | | |
|---|---|---|---|
| 2006/0073048 A1 | 4/2006 | Malackowski | |
| 2007/0258838 A1* | 11/2007 | Drake | F04B 43/0072 |
| | | | 417/477.2 |
| 2011/0060328 A1 | 3/2011 | Skwarek et al. | |
| 2011/0178515 A1 | 7/2011 | Bloom et al. | |
| 2012/0253343 A1 | 10/2012 | McClurken et al. | |
| 2013/0197496 A1 | 8/2013 | Lueckge et al. | |
| 2013/0289678 A1 | 10/2013 | Clark et al. | |
| 2014/0207133 A1* | 7/2014 | Model | A61B 18/1815 |
| | | | 606/34 |
| 2014/0276792 A1* | 9/2014 | Kaveckis | A61B 18/1492 |
| | | | 606/41 |
| 2016/0287779 A1 | 10/2016 | Orczy-Timko et al. | |
| 2018/0326144 A1 | 11/2018 | Truckai | |
| 2020/0060750 A1 | 2/2020 | Kaveckis et al. | |
| 2021/0177654 A1* | 6/2021 | Dunne, Jr. | A61M 3/022 |
| 2021/0212763 A1 | 7/2021 | Condie et al. | |

* cited by examiner

PUMP AND CASSETTE SYSTEM FOR USE IN MICROWAVE ABLATION

FIELD

The present disclosure relates to a pump and cassette system for movement of a cooling fluid. More particularly, the present disclosure relates to a pump and cassette system that can be used as part of a microwave ablation system to move cooling fluid through a microwave ablation probe assembly.

BACKGROUND

This section provides background information related to the present disclosure which is not necessarily prior art.

Ablation apparatuses and systems are used to perform ablation treatments in which a probe is inserted at or near a target tissue in a patient. The target tissue is typically an abnormal tissue such as a tumor or other growth. The ablation treatment is performed to destroy the target tissue to reduce the likelihood of further growth or spreading of the target tissue in the patient. One type of ablation is thermal ablation. In thermal ablation, the probe that is positioned at or near the target tissue causes the temperature of the target tissue, typically in a localized region proximate the probe, to be elevated to a temperature at which the target tissue is destroyed.

The thermal ablation can be induced by the emission of microwaves at or near the target tissue. A microwave generator may be used that sends a microwave signal to an antenna in the ablation probe. The antenna may emit microwave energy into surrounding tissue causing the temperature of such tissue to be elevated to temperatures sufficient to cause thermal ablation.

It can be desirable to move thermal energy that is generated during thermal ablation away from the probe or away from the cables that may operably connect the ablation probe to an ablation console. Existing systems, however, suffer from various drawbacks including complexity, difficulty of use, inefficiency and/or undesirable movement of the ablation probe during treatment. There exists a need, therefore, for improved pump systems that can be easily operated and demonstrate improved performance.

SUMMARY

This section provides a general summary of the disclosure, and is not a comprehensive disclosure of its full scope or all of its features.

The present disclosure provides a cooling system that may be used to cool or remove thermal energy from an ablation probe. The cooling system may be incorporated into a microwave ablation console that can provide a microwave signal to an ablation probe and provide simultaneous thermal management of the ablation probe. The cooling system may include a cassette that can be loaded into a cassette receptacle of an ablation console. A pump assembly may be included to engage a supply tube in the cassette and move coolant through a coolant flow path that includes the ablation probe. The pump assembly can be configured to automatically engage and apply a compression force to the supply tube to provide stable, steady coolant flow in a manner that improves over existing systems.

In some embodiments of the present disclosure, an apparatus for cooling an ablation probe is provided. The apparatus may include a cassette receptacle configured to accept a cassette including a supply tube for supplying a coolant to the ablation probe. The apparatus may also include a pump head movably positioned proximate the cassette receptacle that is configured to move between a loading position and an operating position. The pump head may include one or more rollers configured to engage the supply tube of the cassette when the pump head is in the operating position. The apparatus may also include an actuator coupled to the pump head. The actuator may be configured to move the pump head between the loading position and the operating position.

In one aspect, the cassette receptacle may be positioned in a front face and configured to accept the cassette in a loading direction.

In another aspect, the pump head may be configured to move between the loading position and the operating position along an engagement direction. The engagement direction may be oriented orthogonally to the loading direction.

In another aspect, the loading direction may be a horizontal direction and the engagement direction may be a vertical direction.

In another aspect, the actuator may include a spring and a stepper motor; and the spring may be configured to apply a predetermined force to the supply tube via the pump head when the stepper motor moves the pump head to the operating position.

In another aspect, the actuator may be indirectly coupled to the pump head via one or more arms.

In another aspect, the apparatus may include a first arm and a second arm. The first arm and the second arm may each be connected to the pump head at a first end and each connected at a rotational axis at a second end. The actuator may be positioned between and coupled to the first arm and the second arm.

In another aspect, the apparatus may include an occlusion plate positioned in the cassette receptacle.

In another aspect, the occlusion plate may have an upward-facing concave shape.

In another aspect, the occlusion plate is stationary.

In another aspect, the apparatus may include the cassette.

In another aspect, the cassette may include a case and the case defines an opening and the supply tube extends across the opening.

In another aspect, the cassette may include a chamber positioned inside a case. The chamber may be fluidly connected to the supply tube and the chamber can be configured to dampen pressure oscillations during operation of the pump head.

In another aspect, an inlet to the chamber may be positioned vertically above the outlet of the chamber.

In another aspect, the cassette may include one or more magnets configured to retain the cassette in a desired position in the cassette receptacle.

In another aspect, a retainer may be coupled to the pump and configured to move with the pump head when the pump head is moved from the loading position to the operating position. The retainer can be configured to engage and retain the cassette in the cassette receptacle when the pump head is in the operating position.

In another aspect, a case of the cassette may define an opening to receive the retainer when the pump head is in the operating position.

In another aspect, the supply tube of the cassette is fluidly coupled to a coolant flow path configured to move thermal energy away from a microwave ablation probe.

In another aspect, the cassette may be part of an ablation probe assembly and the ablation probe assembly may also include a cable and an ablation probe.

In another aspect, the apparatus may also include one or more microwave generators configured to deliver a micro-wave signal to a microwave ablation probe.

In some embodiments of the present disclosure, a method for cooling an ablation probe is provided. The method may include accepting a cassette into a cassette receptacle of an ablation console, moving a pump head into engagement with a supply tube of the cassette, and operating the pump head to move coolant through the supply tube.

In one aspect, the step of moving the pump into engage-ment with the supply tube may be automatically performed in response to detecting that the cassette is positioned at a predetermined location in the cassette receptacle.

In another aspect, the step of moving the pump head may include applying a predetermined force to the supply tube.

In another aspect, the method may include receiving an input from a user of one or more operating parameters. The one or more operating parameters may include a rotational speed of the pump head and a force to be applied to the supply tube by the pump head.

In another aspect, the method may include determining one or more characteristics of the cassette and setting one or more operating parameters based on the one or more char-acteristics of the cassette.

In another aspect, the pump head may be moved in an engagement direction that is orthogonal to a loading direc-tion of the cassette into the cassette receptacle.

In another aspect, the method may include retaining the cassette in the cassette receptacle when the pump is moved into engagement with the supply tube.

In another aspect, the method may include adjusting a force applied by the pump head to the supply tube.

Further areas of applicability will become apparent from the description provided herein. The description and specific examples in this summary are intended for purposes of illustration only and are not intended to limit the scope of the present disclosure.

DRAWINGS

The drawings described herein are for illustrative pur-poses only of selected embodiments and not all possible implementations, and are not intended to limit the scope of the present disclosure.

Corresponding reference numerals indicate correspond-ing parts throughout the several views of the drawings.

DETAILED DESCRIPTION

Figure 1:
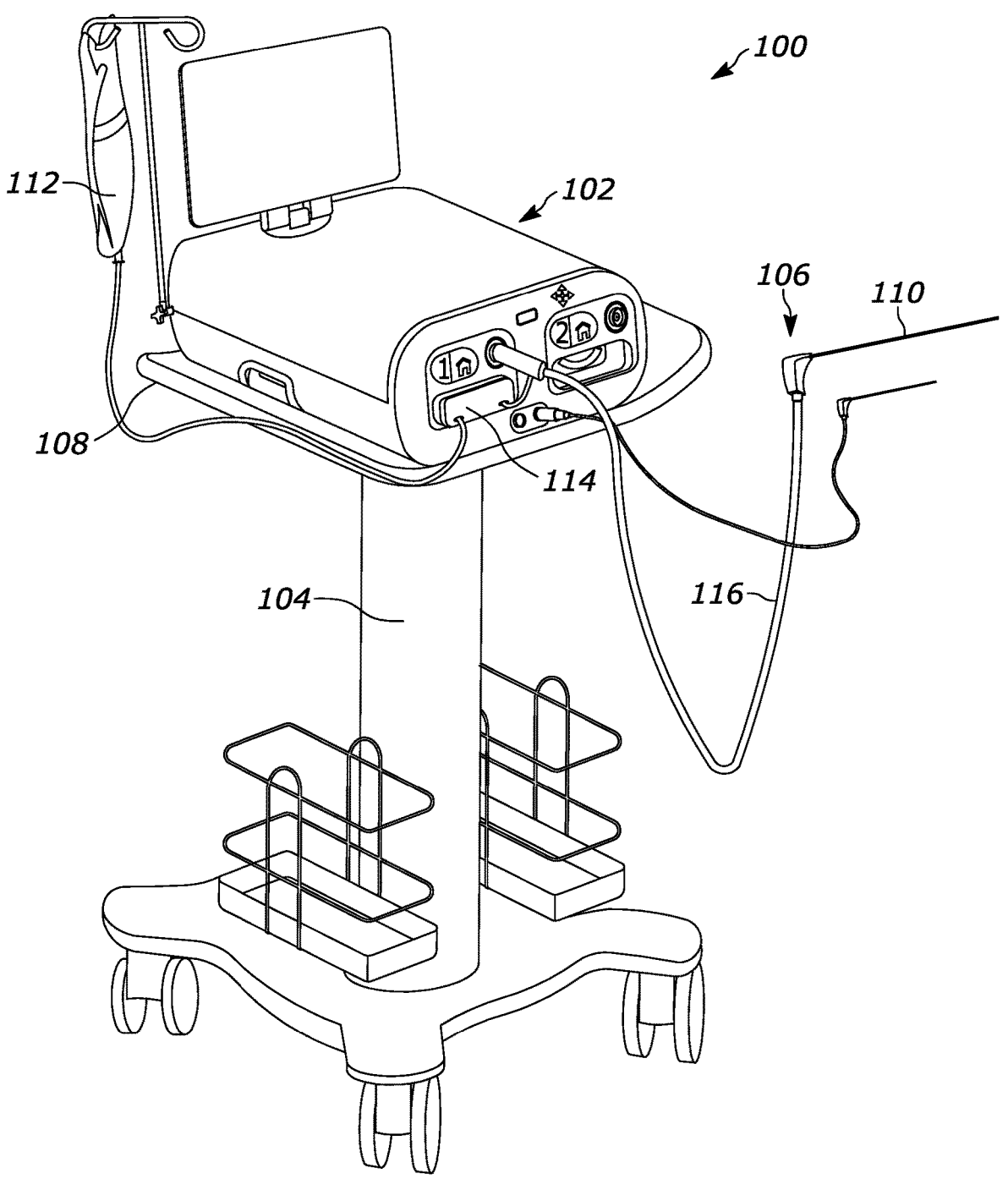
FIG. 1 is an isometric view of an example microwave ablation system in accordance with some embodiments of the present disclosure.

Example embodiments will now be described more fully with reference to the accompanying drawings. For purposes of the description hereinafter, it is to be understood that the embodiments described below may assume alternative variations and embodiments. It is also to be understood that the specific articles, compositions, and/or processes described herein are exemplary and should not be consid-ered as limiting. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orien-tation as then described or as shown in the drawing under discussion. These relative terms are for convenience of description and do not require that the apparatus be con-structed or operated in a particular orientation. Terms con-cerning attachments, coupling and the like, such as "con-nected" and "interconnected," refer to a relationship wherein structures are secured or attached to one another either directly or indirectly through intervening structures, as well as both movable or rigid attachments or relationships, unless expressly described otherwise.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

In the present disclosure the singular forms "a," "an," and "the" include the plural reference, and reference to a par-ticular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" prefer-ably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2

& 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

In some embodiments of the present disclosure, an improved cooling system is provided. The cooling system may be provided as part of a microwave ablation console. The console may include one or more microwave generators configured to deliver a microwave signal to a microwave ablation probe. The cooling system may include a pump and cassette that operate to deliver a cooling fluid to the ablation probe and/or an ablation cable that connects the ablation probe to the console. The cooling fluid can be circulated to remove thermal energy from the ablation probe and/or the ablation cable.

The improved cooling system of the present disclosure overcomes overcome various drawbacks of existing systems and also improves performance, ease of set-up and operation over known systems and methods. In some embodiments, the pump may be integrated into the microwave ablation console and allow the cassette to be easily installed in a proper position to engage the coolant fluid conduit to the pump. The configuration of the present console reduces a likelihood of misalignment or incorrect assembly that can result in inefficient operation or failure.

Existing cooling systems often include a pump mechanism that is a discrete unit separate from the microwave ablation console. This requires increased lengths of cooling fluid conduits and can require operation independent of the operation of the microwave ablation console. Existing cooling system can also require a user to install and position the cooling fluid conduit manually into the pump mechanism. Such manual installation can require a significant amount of time and user experience to perform correctly. Existing systems may also use peristaltic pump assemblies that result in uncontrolled and/or elevated pressure pulses during operation. Such elevated pressure often requires additional relief valves, high-strength or durable materials that can add cost to the assemblies. Still further, the pressure pulses of existing pump assemblies can cause the cooling fluid conduit to physically move with each pressure pulse. Such movement is undesirable because an ablation probe is positioned in a precise location relative to a target tissue and movement of the cooling fluid conduits (that are connected to the ablation probe) can cause movement of ablation probe.

Another drawback of existing systems is the limitation on the length of the cable that may be used to couple the microwave ablation probe to the ablation base unit. Existing designs require the ablation base unit to be positioned close to the patient and to other equipment located in the treatment environment. This may make the ablation treatment more difficult given a lack of space in the treatment environment. The cooling systems of the present disclosure allow greater and adjustable pumping pressures to be achieved that allows the cables used to couple the microwave ablation probe to the base to be lengthened. In some examples, the cooling systems of the present disclosure may allow the cables to exceed 10 feet in length. Such a length is not possible using existing designs and methods. As further described below, the cooling systems of the present disclosure overcome these drawbacks of existing systems.

Referring now to FIG. 1, an example microwave ablation apparatus 100 is shown. The microwave ablation apparatus 100 may include a portable base unit or console 102, a cart 104, and an ablation probe assembly 106. The console 102 can be positioned on the cart 104. As will be further described, the console 102 may include a microwave generator and a coolant pump. In some embodiments, the ablation apparatus 100 may have a structure and functionality described in U.S. Patent Application No. TBD, titled PORTABLE ABLATION APPARATUS AND RELATED METHODS OF USE, filed on the same day as the present application to Varian Medical Systems, Inc. The contents of this application are incorporated by reference herein in its entirety. In various embodiments, the ablation apparatus 100 can be operated to perform ablation treatments by sending a microwave signal to an antenna in an ablation probe 110 via cable 116. The antenna may deliver the microwaves to a target tissue at or near the ablation probe 110. The microwaves may induce an elevated temperature at the target tissue to destroy the target tissue.

During the ablation treatment, the ablation apparatus 100 may also deliver a cooling fluid or coolant from a coolant receptacle 112 to the probe 110 using the coolant pump positioned inside the console 102. A coolant cartridge or cassette 114 may be inserted into the front face of the console 102 and engage the pump to move the coolant from the coolant receptacle 112 to the probe 110 through the cable 116. The movement of the coolant may absorb thermal energy from the cable 116 and/or probe 110 effectively cooling the cable 116 and/or portions of the probe 110.

As can be seen, the console 102 and the cart 104 can be easily moved in a hospital, treatment center, or other environment. The cart 104 may include a support surface such as platform 108 that is positioned at an elevated position above the floor to allow access to the functionality of the system. The platform 108 may be positioned, for example, at a height approximately the same as a treatment height of a patient. The patient that is undergoing an ablation treatment may be, for example, positioned on a bed of an imaging system. The imaging system may be a CT scanner, MRI machine, X-ray apparatus or other imaging device. With the console 102 positioned at a height approximately equal to that of the bed of the imaging system, the ablation treatment can be more easily performed. In addition, the console 102 can be moved next to the bed so that the length of the cables 116 that may be required to deliver microwave signals and/or coolant from the base unit to the probe 110 can be reduced over ablation systems that are more cumbersome or may need to be located at other positioned in the treatment environment.

Figure 2:
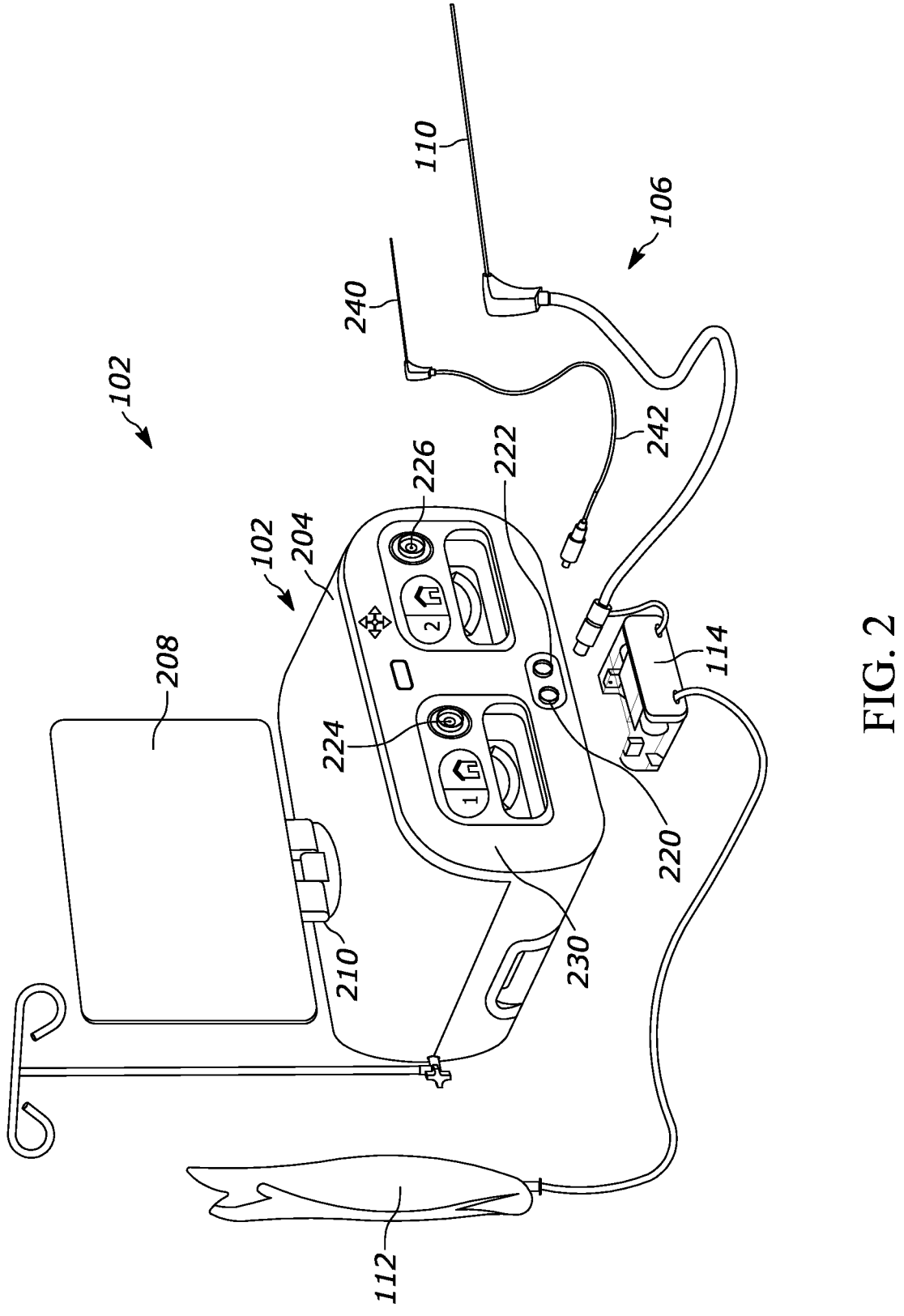
FIG. 2 is an isometric view of an example microwave ablation console and ablation probe assembly that can be part of the microwave ablation system of FIG. 1.

The console 102 can be portable in that it can be lifted and moved by one user. The console 102 can be removed from the cart 104 and be positioned on a table, counter, or other surface in a treatment or laboratory setting. The console 102 may include a housing 204 (FIG. 2) that is positioned around the inner components of the console 102. The housing 204 may include one or more walls that define an interior volume in which the inner components are located. As shown in FIG. 2, the console 102 may include a first microwave port 224, a second microwave port 226, a first sensor port 220, and a second sensor port 222. The console 102 may also include a display 208 to allow input from a user and to display one or more operating parameters of the console 102.

The first microwave port 224 and the second microwave port 226 can be similarly configured and can be an electrical connector to allow a mating connector to electrically couple the ablation probe assembly 106 to a respective microwave generator positioned inside the housing 204. In some examples, the first microwave port 224 may include a first marking and the second microwave port 226 may include a second marking. The first marking and the second marking may be different to allow a user to differentiate between the ports. The first marking and the second marking may include various suitable identifiers such as a color, a symbol, a letter, a number, a shape, a colored light or others. In some examples, the first marking and the second marking may include multiple identifiers from the previous list of identifiers. The first marking and the second marking can be used so as to guide an operator in the set-up and use of the console 102 to ensure that the proper connections are made by the operator. In some embodiments, the ablation probe assembly 106 may have a structure and functionality described in U.S. Patent Application No. TBD, titled MICROWAVE ABLATION PROBE ASSEMBLY AND CABLE STRUC-TURE, filed on the same day as the present application to Varian Medical Systems, Inc. The contents of this application are incorporated by reference herein in its entirety.

The first microwave port 224 and the second microwave port 226 may be positioned in a front face 230 of the housing 204. This may allow a user to easily connect an ablation probe assembly 106 to the first microwave port 224 and/or the second microwave port 226. In other examples, the first microwave port 224 and the second microwave port 226 may be positioned at other locations in the housing 204 such as in the side walls, or top surface of the housing 204. While the example console 102 shown in FIG. 2 includes two microwave generators and two microwave ports, it should be appreciated that one generator and port may be included in some examples and more than two generators and ports may be included in other examples.

As further shown in this example, the console 102 may include a first sensor port 220 and a second sensor port 222 positioned on the front face 230. This positioning can allow an operator to easily connect one or more sensors 240 to the console 102. As shown in FIG. 2, the ablation probe assembly 106 may include a sensor probe 240. In some examples, the sensor probe 240 may be provided independently from the ablation probe assembly 106. In other examples, the sensor probe 240 may be provided with the ablation probe assembly 106. The sensor probe 240 may be positioned at or near the target tissue in the patient during an ablation treatment to monitor and/or determine one or more parameters. For example, the sensor probe 240 may include one or more measurement points that can measure an impedance, temperature, moisture, density, or other characteristics of the patient. This measurement information can be transferred via a sensor cable 242 to the console 102. The sensor cable 242 may terminate at a sensor connector that can be connected to the console 102 at the first sensor port 220 and/or the second sensor port 222. This information can be sent to a processor, memory, or other element in the console 102 to be stored and/or displayed on the display 208. While the example console 102 includes two sensor ports 220, 222, it should be appreciated that the console 102 may include less than two sensor ports or more than two sensor ports in other examples.

Figure 3:
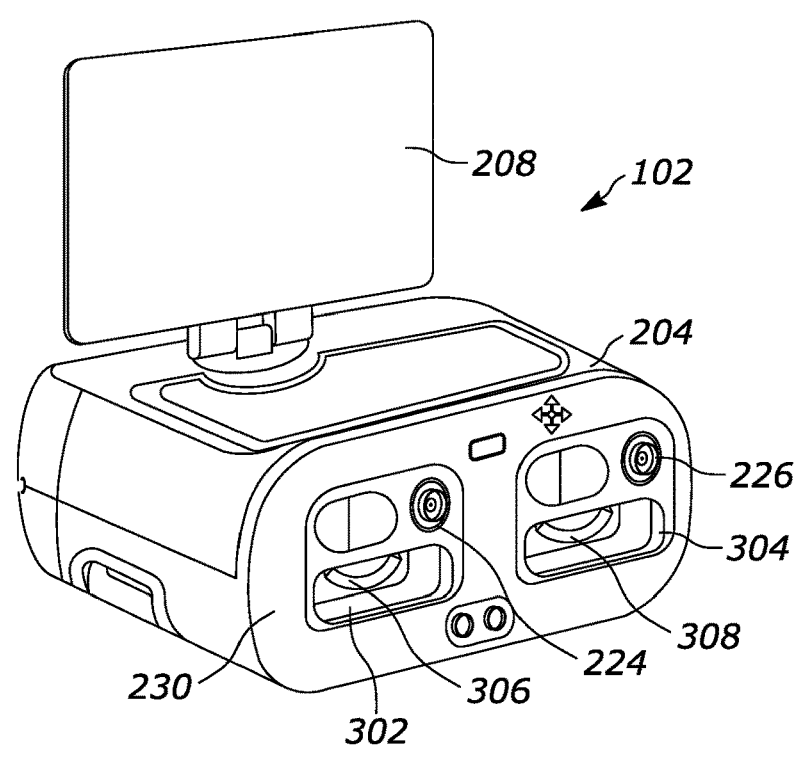
FIG. 3 is an isometric view of the example microwave ablation console of FIG. 2.

Referring now to FIG. 3, the console 102 may include one or more cassette receptacles. In the example shown, the console 102 includes a first cassette receptacle 302 and a second cassette receptacle 304. It should be appreciated that other examples may include more than two cassette receptacles.

The first cassette receptacle 302 and the second cassette receptacle 304 are configured similarly in the example shown. The first cassette receptacle 302 and the second cassette receptacle 304 are shaped in a similar manner to the cassettes that will be described further later. With such complimentary shape, one cassette can be inserted into each of the first cassette receptacle 302 and/or the second cassette receptacle 304. In this example, the first cassette receptacle 302 and the second cassette receptacle 304 each have a rounded rectangular shape and are inset into the front face 230 of the console 102. One or more walls of the first cassette receptacle 302 and the second cassette receptacle 304 define an inwardly protruding cavity in the front face 230. A cassette can be inserted into the cavity and be retained in a desired position. The cavity may include detents, magnets, clips, locks or other retention features to secure the cassette in the cavity while still allowing a user to remove or install the cassette into the cavity.

Figure 4:
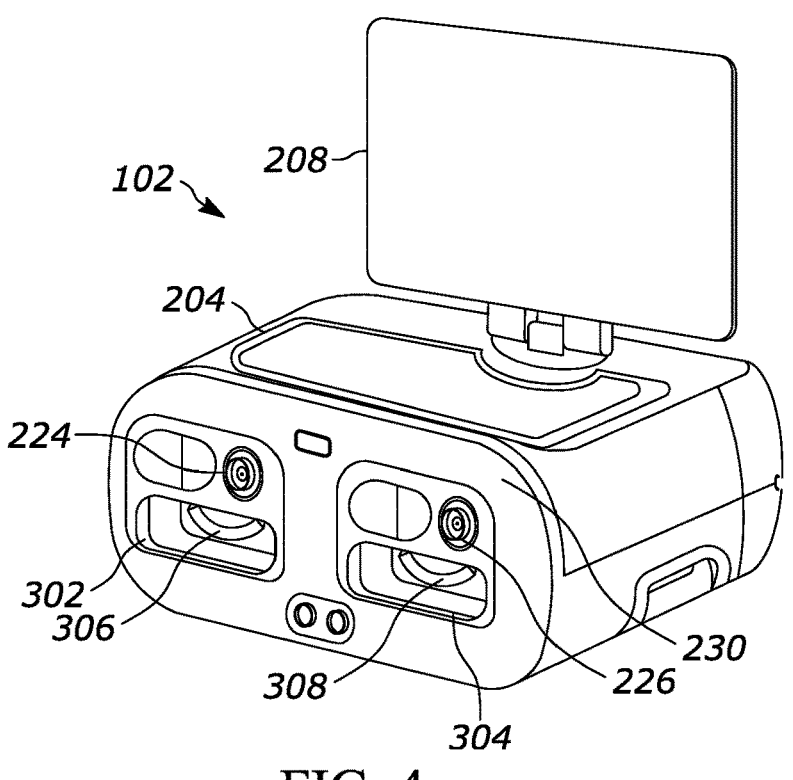
FIG. 4 is another isometric view of the example micro-wave ablation console of FIG. 2.

As further shown in FIGS. 3 and 4, the first cassette receptacle 302 and the second cassette receptacle 304 may include a first occlusion plate 306 and a second occlusion plate 308, respectively. The first occlusion plate 306 may be positioned on an inner vertical wall of the first cassette receptacle 302. The second occlusion plate 308 may be positioned on an inner vertical wall of the second cassette receptacle 304. When a cassette is positioned in the first cassette receptacle 302, the walls of the cavity guide the cassette into a desired position and align a supply tubing 1004 (FIG. 10) of the cassette into the proper position such that the supply tubing 1004 over the first occlusion plate 306. The second cassette receptacle 304 and the second occlusion plate 308 are similarly configured. The occlusion plates 306, 308 may have an upward facing concave shape and be stationary on the console 102.

Figure 5:
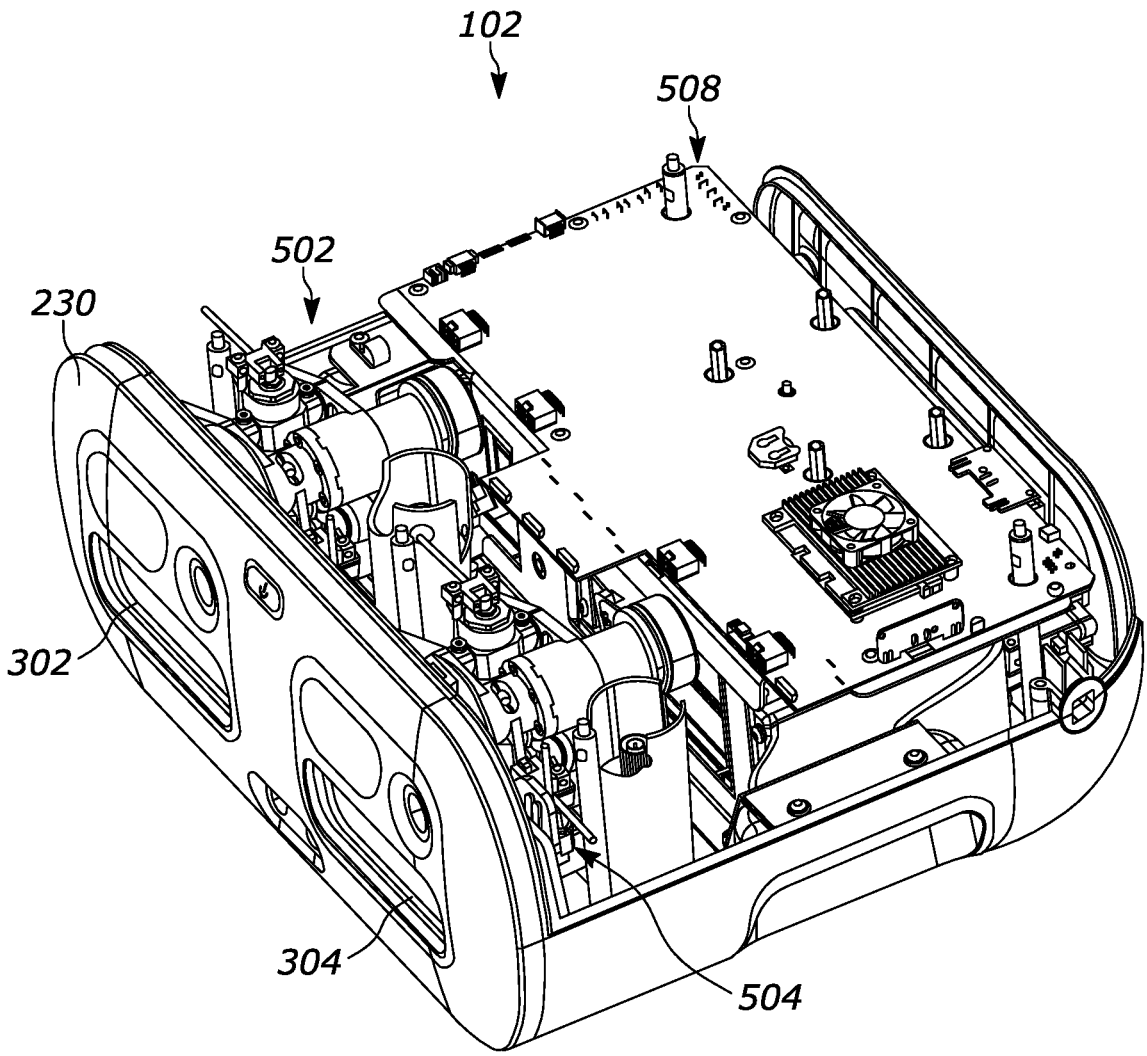
FIG. 5 is an isometric view of the example microwave ablation console of FIG. 2 shown with an upper portion of the shell removed.

Turning now to FIG. 5, a console 102 is illustrated with a portion of the outer shell removed to allow the inner elements of the console 102 to be viewed. As can be seen, a first pump assembly 502 is positioned to operatively engage a first cassette (not shown) that may be inserted into the first cassette receptacle 302. The console 102 may also include a second pump assembly 504 that is positioned to operatively engage a second cassette (not shown) that may be inserted into the second cassette receptacle 304. The first pump assembly 502 and the second pump assembly 504 may be coupled to a control board 508. The control board 508 may include one or more processors, memory, and other control elements to allow the functionality of the pump assemblies 502, 504 to be controlled via the display 208 (FIG. 2) that can allow a user to input, view, modify, and operate various parameters and functions of the pump assemblies 502, 504. The first pump assembly 502 and the second pump assembly 504 are independent from each other and can be operated separately or simultaneously as may be desired for a particular treatment. The settings, parameters, and operation of the first pump assembly 502 and the second pump assembly 504 can be set and operated with the same or similar operating conditions in some instances. In others, the settings, parameters, and operation of the first pump assembly 502 and the second pump assembly 504 can be different.

Referring now to FIGS. 6 to 9, the first pump assembly 502 is shown. In the description below, the first pump assembly 502 is described but it should be appreciated that the second pump assembly 504 includes the same or similar elements and can provide the same functions as first pump assembly 502. The second pump assembly 504 is not described separately for the sake of brevity.

Figure 6:
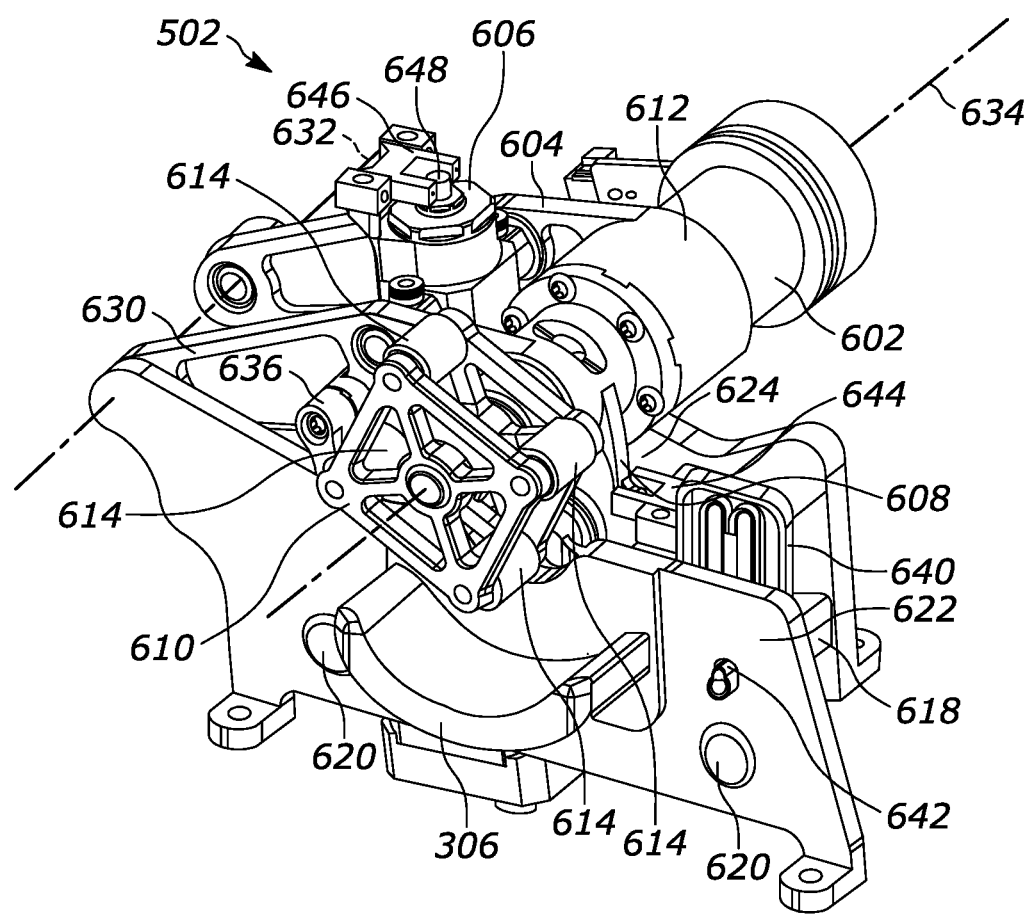
FIG. 6 is an isometric view of an example pump assembly of the present disclosure shown in a raised or loading configuration.
Figure 7:
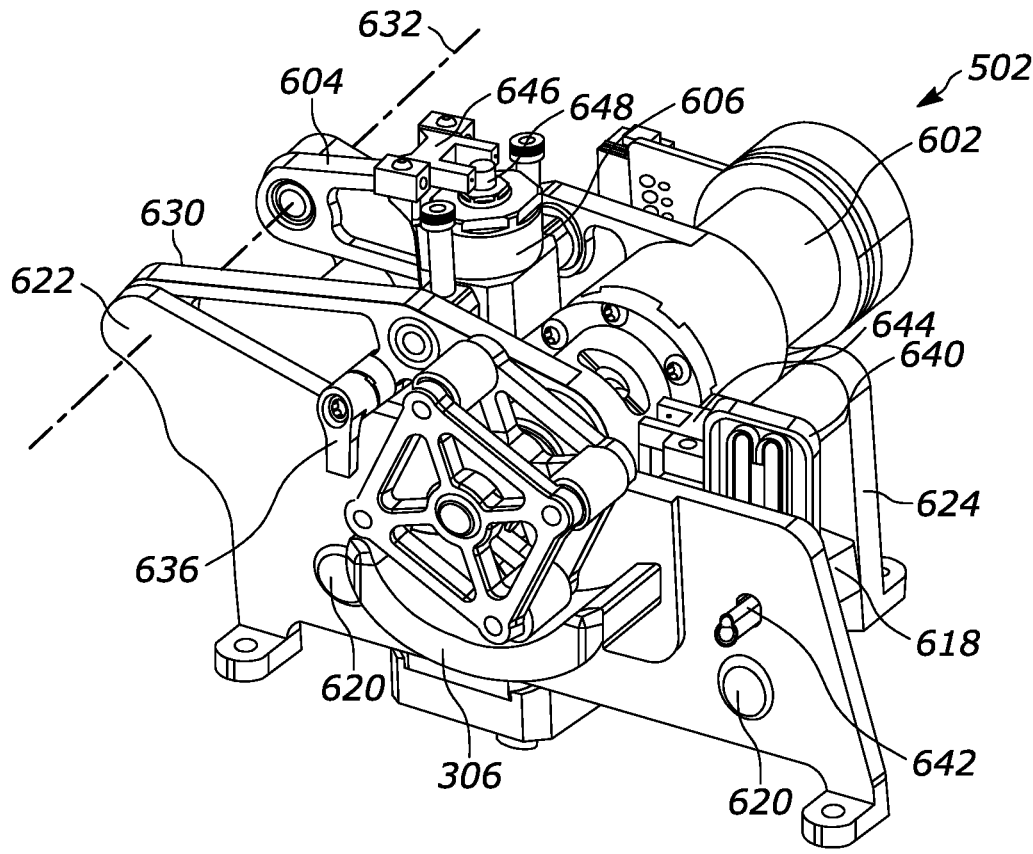
FIG. 7 is an isometric view of the pump assembly of FIG. 6 shown in a lowered or operating configuration.

The first pump assembly 502 may include a pump head 602 and an actuator 606. The pump head 602 may be coupled to the actuator 606 by one or more arms to allow the pump head 602 to move relative to the occlusion plate 306. FIG. 6 illustrates the pump head 602 in a loading (or raised) position and FIG. 7 illustrates the pump head 602 in an operating (or lowered) position. In the example shown, the pump head 602 is coupled to the actuator 606 via a first arm 630 and a second arm 604. The first arm 630 is positioned on a front side of the actuator 606 (closer to the occlusion plate 306) and the second arm 604 is located on a back side of the actuator 606 (away from the occlusion plate 306. In this configuration, the actuator 606 is positioned between the first arm 630 and the second arm 604.

As will be further described below, the actuator 606 moves the first arm 630 and the second arm 604 upwards and downwards that, in turn, causes movement of the pump head 602 in a vertical direction. As shown, the actuator 606 is connected to the first arm 630 and the second arm 604 at a position between an axis of rotation 632 at one end of the arms and the pump head 602 positioned at the opposite end of the arms 630, 604. The first arm 630 and the second arm 604 are connected to a first support 622 and a second support 624 at the axis of rotation 632. The first support 622 may also form a back wall of the cassette receptacle 302 (FIG. 3). The first support 622 may be vertically positioned as shown. In addition, the occlusion plate 306 may be coupled to the first support 622 or be integrally formed with the first support 622.

The second support 624 can be oriented substantially parallel to but spaced apart from the first support 622. In this example, the second support 624 is located behind (in a direction away from the occlusion plate 306) the first support 622. The second arm 604 may be connected to the second support 624 at the axis of rotation 632.

The first support 622 may also include and/or support other elements of the pump assembly 502. The first support 622 may include one or more magnets 620. The magnets 620 may be positioned on a face of the first support 622 and be located at or around the occlusion plate 306. In the example shown in FIG. 6, the first support 622 includes two magnets 620 with each magnet positioned on opposite lateral sides of the occlusion plate 306. The magnets 620 can be positioned to retain the cassette in a desired position when the cassette is inserted into the cassette receptacle 302 (FIG. 3). The cassette may include a ferrous tab that mates to the magnet 620. In other examples, the cassette may include a mating magnet oriented with a mating/facing/interfacing polarity opposite to the magnet 620. The magnet 620 can position and retain the cassette in a desired position during loading of the cassette into the cassette receptacle 302 (FIG. 3).

The first support 622 may also include a cassette sensor 618. The cassette sensor 618 can be mounted to the first support 622. The cassette sensor 618 operates to determine when a cassette has been inserted into position in the cassette receptacle 302. The cassette sensor 618 may be a proximity sensor, optical sensor, or the like. The first support 622 may include an opening through which a cassette pin 642 may be positioned. The cassette pin 642 may be biased to protrude through the opening in the first support 622. When the cassette is positioned in the cassette receptacle 302, the cassette pin 642 may be pushed in a direction away from the occlusion plate 306 (i.e., in a direction toward the interior of the console). The cassette sensor 618 may positioned at or around the cassette pin 642 and may determine whether the cassette is seated in the cassette receptacle by determining a position of the cassette pin 618. The cassette pin 618 may be integrally formed with or connected to a swing arm 640. The swing arm 640 may be mounted to the first support 622. The cassette pin may extend downward from the swing arm 640 and be positioned in the opening of the first support 622. the cassette sensor 618 can determine whether a cassette has been positioned at the first support 622. In the example shown, the cassette sensor 618 is positioned on a lateral side occlusion plate 306. In other examples, the cassette sensor 618 may be located at other locations. In other examples, the cassette sensor 618 may be positioned at other locations and have other configurations.

The pump assembly 502 may also include a cassette retainer 636 and a position flag 608. The cassette retainer 636 operates to retain the cassette in the cassette receptacle after the pump head 602 is lowered into the operating position (FIG. 7). The cassette retainer 636, in the example shown, is connected to the first arm 630 and projects downward in a vertical direction toward the occlusion plate 306. The cassette retainer 363 is configured to insert into a complimentarily shaped opening or depression in the cassette. When the cassette retainer 636 moves downward into the opening or depression in the cassette, the cassette cannot be removed from the cassette receptacle until the pump assembly 502 is raised back to the loading position (FIG. 6). The cassette retainer 636 can prevent the cassette from being dislodged and/or the coolant tubing from being displaced during operation that could damage the cassette or the pump assembly 502. In addition, the cassette retainer 636 prevents undesirable relative movement of the cassette that could negatively impact the flow of coolant to the ablation probe during operation.

The position flag 608 operates to provide positioning information regarding a vertical position of the pump head 602. The position flag 608 extends away from the pump head 602 and toward a position sensor 644. The position sensor 644 operates to determine a position of the position flag 608. The position sensor 644 may be mounted proximate the position flag 608 on a mount 616. The position sensor 644 may be an optical sensor, proximity sensor or the like that can determine a location and/or position of the position flag 608. As will be further described below, the pump head 602 can be vertically moved to a desired vertical position relative to the occlusion plate 306. The position flag 608 and the position sensor 644 operate to provide feedback as to the location of the pump head 602 and/or the movement of the pump head 602 from its loading position (FIG. 6) to an operating position (FIG. 7). In other examples, the pump assembly 502 may include other sensors and/or may have different position flags to provide information regarding the movement and/or location of the pump head 602.

The pump head 602, in the example shown, operates as a peristaltic pump. The pump head 602 may include a motor 612 and a roller head 610. The motor 612 may be coupled to the roller head 610 to rotate the roller head at a predetermined rotational speed. This functional coupling may include a gear box between the motor and the roller head to scale the speed and torque of the motor to a desired speed and a desired torque. The motor 612 can be any suitable electronically controlled electric motor that can be adjusted to spin the roller head 610. The roller head 610 include multiple rollers 614 located at various intervals around the roller head 610. In the example shown, the roller head 610 includes four equally spaced rollers 614. In other examples, the roller head 610 may include more than four rollers, or less than four rollers. The rollers 614 may be spaced at 90 degree intervals around a center of the roller head 610. When the roller head 610 is lowered to the predetermined operational height relative to the occlusion plate 306 (FIG. 7), the rollers 614 are positioned at a predetermined gap from the top surface of the occlusion plate 306. When the roller head 610 is rotated by motor 612, the rollers 614 squeeze a supply tube of the cassette between an outer surface of the rollers 614 and a top surface of the occlusion plate that moves coolant located inside the supply tube. A flow and pressure of the coolant in the supply tube can be adjusted by varying the gap between the roller 614 and the occlusion plate 306, a force applied by the rollers 614 to the supply tube, and by the rotational speed of the roller head 610.

Figure 8:
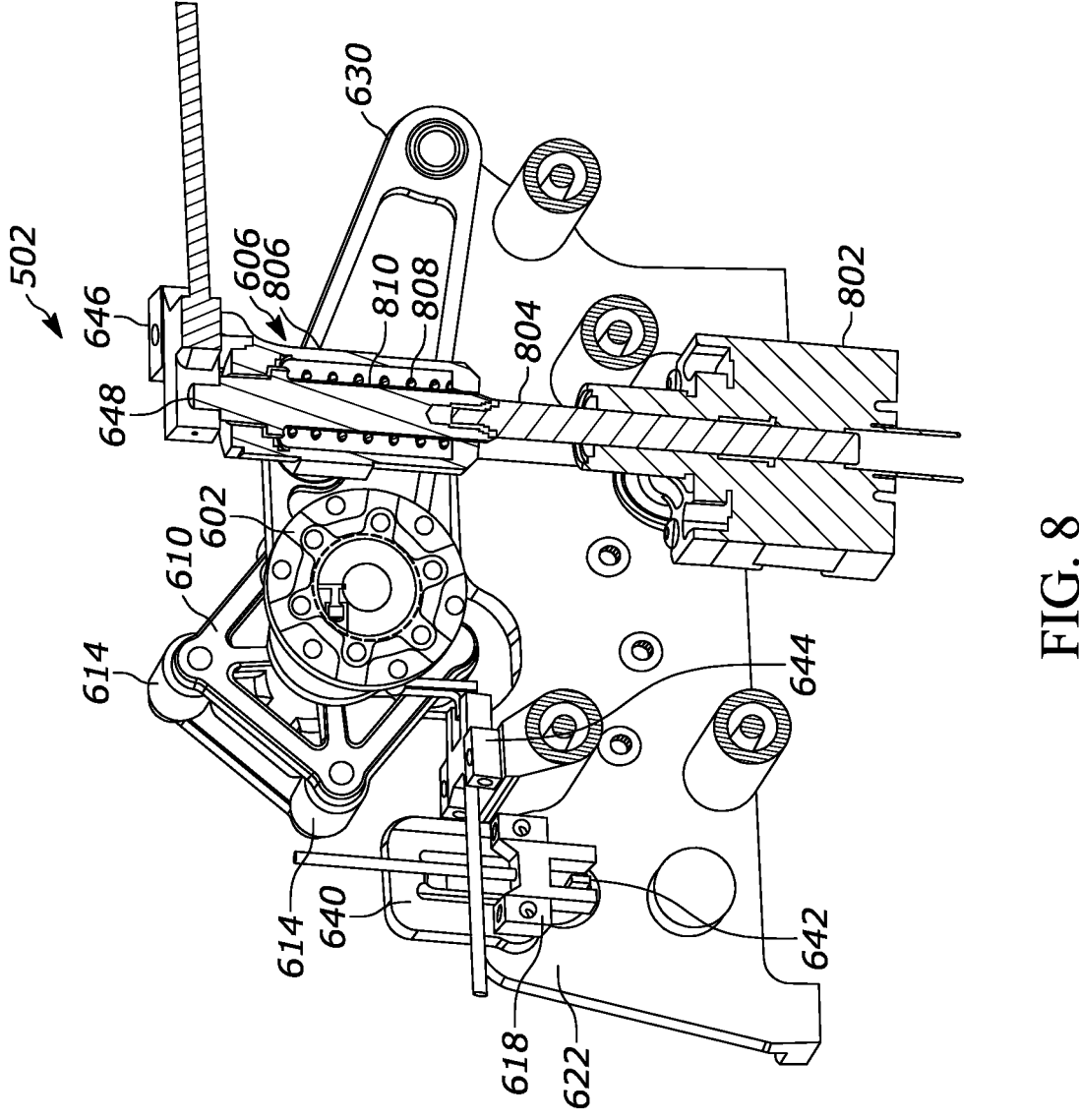
FIG. 8 is a rear partial cross-sectional view of the pump assembly of FIG. 6.
Figure 9:
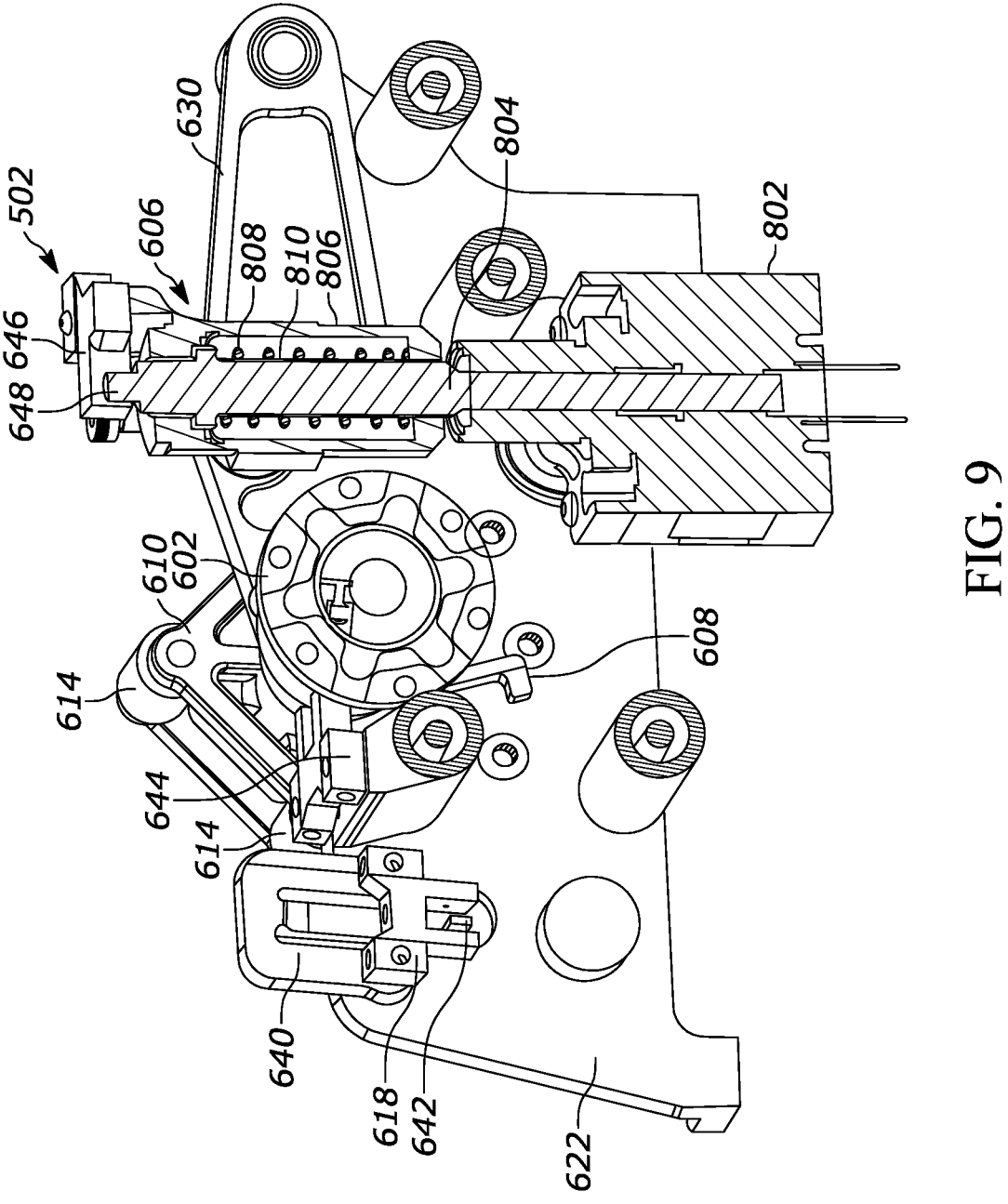
FIG. 9 is a rear partial cross-sectional view of the pump assembly of FIG. 7.

Turning now to FIGS. 8 and 9, the pump assembly 502 is shown as a partial cross-sectional view from a back side thereof with the section plane cut through the actuator 606. From this view the components of the actuator 606 can be viewed as well as a back side of the first support 622. The actuator 606, in the example shown, includes a motor 802, a shaft 804, a spring housing 806, a spring 808, and a compression member 810. The motor 802 may be various suitable motors that can move the shaft 804 to cause the first arm, and thus the pump head 602, to be moved toward and away from occlusion plate 306 (FIG. 6). The motor 802 may be a stepper motor such that the movement of the shaft can be accurately controlled and the actuator 606 can accurately position the pump head 602 in a predetermined position.

The motor 802 is connected to the shaft 804 that, in turn, is connected to the compression member 810. The shaft 804, for example, may include a threaded portion that mates to a complimentary threaded portion of the compression member 810. When the motor 802 rotates the shaft 804, the compression member 810 can be drawn downward toward the motor 802. When the motor 802 rotates in an opposite rotational direction, the compression member 810 can be moved upward in a direction away from the motor 802. The compression member 810 can be indirectly coupled to the first arm 630 and the second arm 604 (not shown), through the spring 808 and the actuator housing 806, to cause movement of the pump head 602 when the compression member 810 is moved by the motor 802 while the pump head 602 is above its operating position. The motor 802 can be controlled by the control board or other control mechanism to accurately position the pump head 602 in a desired position.

In some examples, motor 802 is a stepper motor. In other examples, motor 802 may alternatively include a linerar actuator, worm drive, or other mechanism that may translate shaft 804 and compression member 810 without rotation.

After the roller head 610 of the pump assembly 502 is lowered to the operating position, the additional lowering of the compression member 810 causes the rollers 614 to apply a force to the supply tube that is positioned on the occlusion plate 306. The magnitude of the force that is applied by the rollers 614 can be controlled and varied using the actuator 606. The spring 808 is positioned in the housing 806 and is coiled around the compression member 810. When the compression member 810 is pulled/lowered by the motor 802 while the pump head 602 is in the operating position, the compression member 810 moves downward relative to the housing 806, compressing the spring 808 in a longitudinal direction along the axis of the compression member 810 and the spring 808. The force applied by the rollers 614 can be adjusted or varied according to the amount of longitudinal compression of the spring 808. The spring 808 can be selected with a predetermined spring constant. Thus, when spring 808 is compressed a predetermine longitudinal distance, the force applied by the rollers can be determined. The control board or other controller can be configured to display the applied force and to allow a user to adjust the force applied by the rollers 614. Such inputs and/or controls may be displayed via a user interface on the display 208 (FIG. 2).

The actuator 606 is shown as one example of actuators that may be used in the pump assembly 502. In other examples, the actuator 606 may include a solenoid, pneumatic or electronic cylinder, a linear actuator or other mechanism to move the pump head 602 to a predetermined location and apply a force via rollers 614. In still other examples, the pump head 602 can be variably positioned and controlled using a screw drive, a pulley drive, and/or a straight motor positioned at the fulcrum of the first arm or the second arm. The pump assembly 502 may also include one or more sensors to determine a force and or distance that the pump head 602 is moved or applies to the supply tube. Such sensors may include a linear or rotational potentiometer or hall effect sensors.

In the example shown, the actuator 606 may include a position sensor 646 mounted at or near a top of the housing 806. An actuator pin 648 may extend upward from the compression member 810 or from other part of actuator 606. The actuator pin 648 may be positioned at or near position sensor 646. The position sensor 646 may determine a position and/or movement of the compression member 810 relative to the housing 806. This positional information may be used to determine a location of the pump assembly 502 and/or determine a force applied by the rollers 614.

Figures 10, 11:
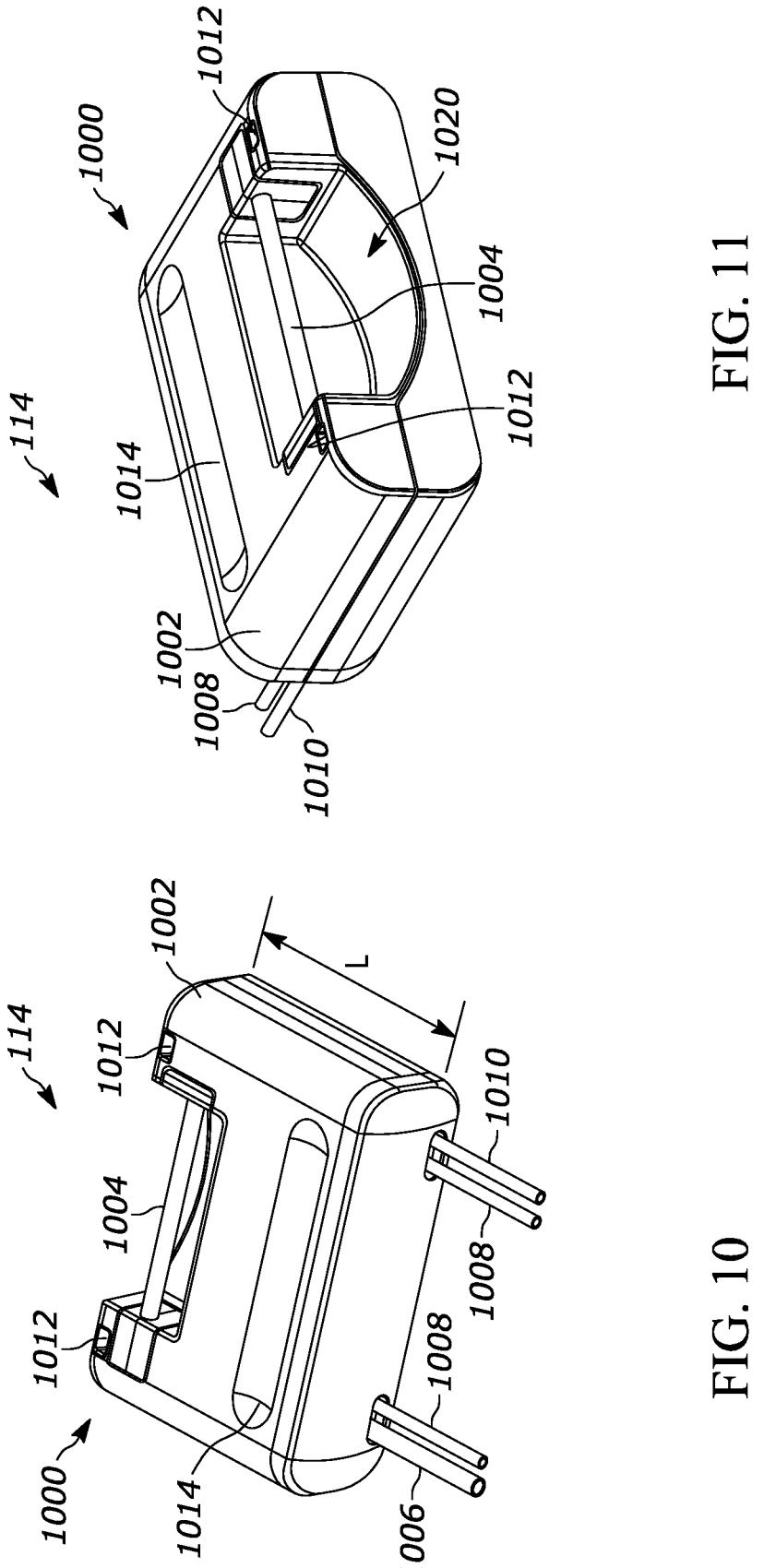
FIG. 10 is an isometric front view of an example cassette of the present disclosure.
FIG. 11 is an isometric rear view of the cassette of FIG. 10.
Figure 12:
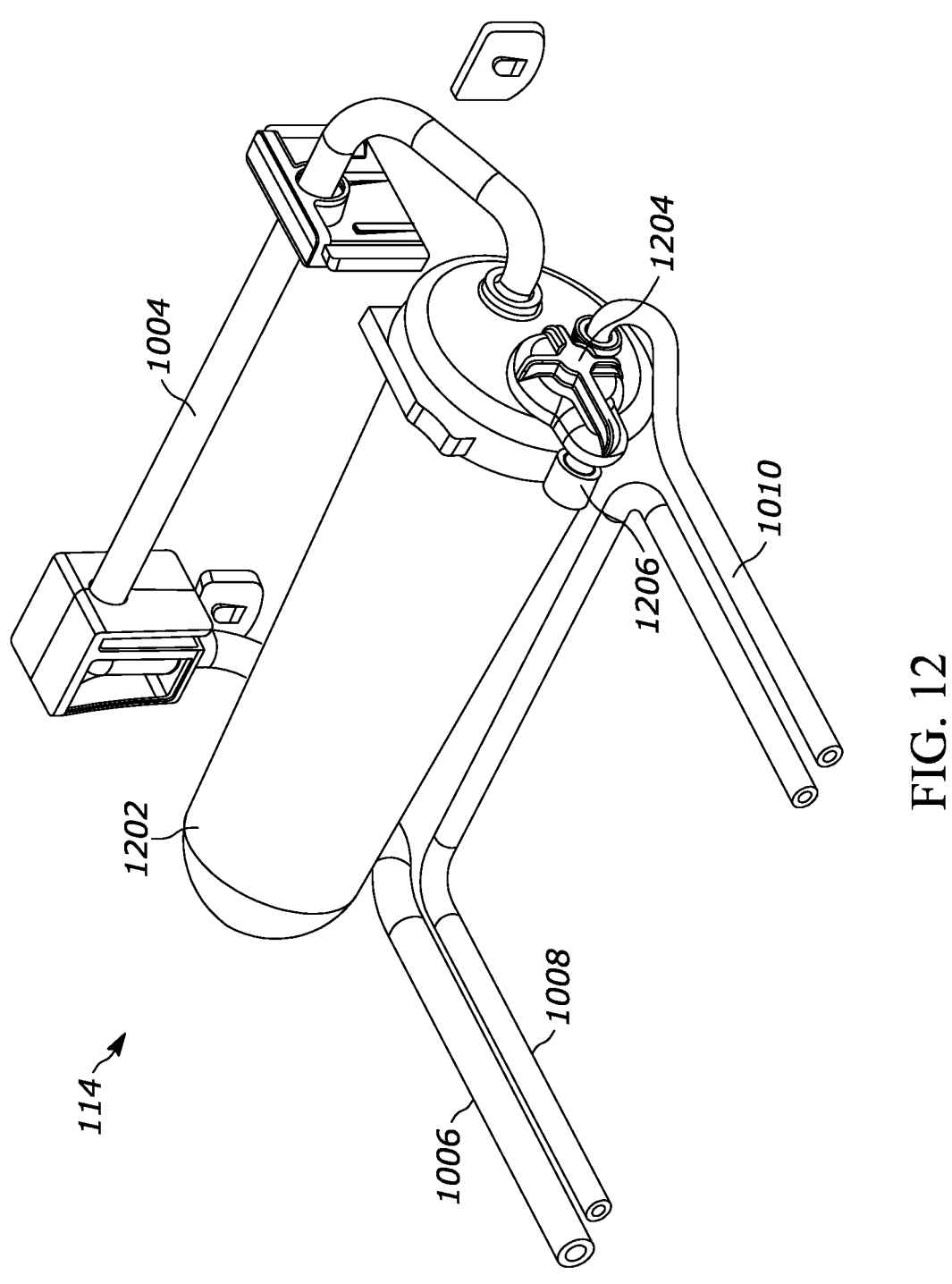
FIG. 12 is an isometric view of the cassette of FIGS. 10 and 11 shown with the housing removed to show the internal elements.

Referring now to FIGS. 10 to 12, an example cassette 114 is shown. The cassette 114 may include a case 1002, a supply tube 1004, an inlet tube 1006, a recirculation tube 1008, and an outlet tube 1010. The case 1002 of the cassette 114 may be sized and shaped to correspond to the size and shape of the cassette receptacle 302 previously described. In this example, the case 1002 has a rounded rectangular shape. The case 1002 may have a length L that is greater than a depth of the cassette receptacle 302. The case 1002 may protrude from the cassette receptacle 302 when the cassette 114 is inserted into the cassette receptacle 302. To facilitate and allow a user to grip and manipulate the cassette 114, the case 1002 may include groove 1014 that may be inset from an upper surface of the case 1002. In other examples, the case 1002 may include other gripping features such as ribs, inlaid rubber to tacky materials or the like.

The case 1002 may also include one or more openings 1012. The openings 1012 may be positioned at or near a distal side of the cassette 114 that is inserted into the cassette receptacle 302. The openings 1012 may be sized and positioned to allow the cassette retainer 636 (FIG. 6) to engage the opening 1012 and retain the cassette 114 in the cassette receptacle 302 when the pump head 602 is in the operational or lowered position. The openings 1012 may be configured as a hole in the case 1002 or may be defined by a recess in the case wall. The case 1002 may be made of any suitable material such as a molded plastic material or the like.

The case 1002 may also include a notched opening 1020 that is sized to permit the supply tube 1004 to be exposed and to allow the occlusion plate 306 to be positioned under the supply tube 1004 when the cassette 114 is fully inserted into the cassette receptacle 302. The opening 1020 may also allow the roller head 610 to engage the supply tube 1004. The lateral sides of the case 1002 may support the supply tube 1004 at opposite sides of the opening 1020 and permit the rollers 614 of the roller head 610 to compress the supply tubing 1004 against the occlusion plate 306 during operation of the pump assembly 502.

Such movement of the roller head 610 moves coolant through the supply tubing 1004. The supply tubing 1004 may be part of a coolant flow path that allows coolant (e.g., water, saline, or the like) to flow through to the ablation probe to transfer thermal energy away from the ablation probe and/or the probe cable 116 during an ablation treatment. The coolant flow path may also allow the coolant to be moved away from the ablation probe 110 and be mixed with coolant from the receptacle 112 and/or be recirculated through the coolant flow path.

Referring now to FIG. 12, internal elements of the cassette 114 are shown. The cassette 114 is illustrated with the case 1002 removed to illustrate the further internal elements of this example cassette 114. The coolant may be introduced to the coolant flow path from the receptacle 112 (FIG. 2). The receptacle 112 may be a bag a saline, for example. The coolant may move from the receptacle into the cassette through the inlet tube 1006. The inlet tube 1006 may be fluidly connected to the supply tube 1004. The inlet tube 1006 and the supply tube may be a common length of tubing. In other examples, the inlet tube 1006 may be coupled to the supply tube 1004 at an elbow so that the tubing may extend substantially horizontally across the opening 1020 of the cassette 114, and/or so that the supply tube 1004 may be a different material optimized for durability and functionality in the pump assembly 502.

During operation of the pump assembly 502 (FIG. 7), the rollers 614 may compress the supply tubing 1004 and cause the coolant to flow from the supply tube 1004 to the chamber 1202. The chamber 1202 may be a hollow container that is initially filled with air. The chamber 1202 may act as an air dampener to prevent and/or minimize the cyclical pressure oscillations in the coolant flow path. Pressure oscillations may be caused by the alternating engagement and disengagement of individual pump rollers 614 against the supply tube 1004 and occlusion plate 306. Inconsistent rotational speed of the pump roller heat 610 depending on the relative position(s) of the roller(s) 614 along the occlusion plate 306, or other causes, can cause oscillations and physical movement of the coolant tubing. Such movement of the coolant tubing is undesirable because it can be distracting to users of the ablation system. The movement can also make it difficult to position the ablation probe 110 at the target tissue and/or to maintain the ablation probe 110 at the target tissue.

The chamber 1202, initially filled with air, allows pumped coolant to enter, which initially displaces some chamber air, pushing the displaced air out outlet tube 1010. Since the coolant is more dense than air, the coolant will move to a lower portion of the chamber 1202 and the air will rise to the top of the chamber, such that the coolant cannot displace the air at the top of the chamber (gravitationally above the inlet and outlet ports) and this air remains trapped in the chamber. The trapped air may act as a dashpot to resist movement and/or backflow of the coolant in the coolant flow path. This can act to resist pressure oscillations in the coolant flow path.

The coolant may exit the chamber 1202 at a position vertically lower than the input to the chamber 1202. The coolant may exit the chamber 1202 through outlet tube 1010 where it can flow to the ablation probe 110 through cable 116. The chamber 1202 may also include a pressure relief valve 1204. The pressure relief valve 1204 may allow coolant to be expelled from the chamber should the pressure in the chamber rise above a predetermined pressure threshold. While not shown, the valve outlet 1206 may be joined to the recirculation tube 1008 via a T or Y connection, rather than having the coolant leak into the cassette 114 and potentially damage console 102.

After the coolant is supplied to the cable 116 and the probe 110 of the ablation probe assembly 106, the coolant may return via a return tubing to the recirculation tube 1008. The recirculation tube 1008 may be fluidly connected to the receptacle 112 and/or to the inlet tube 1006 where the coolant that is at an elevated temperature may mix with coolant in the receptacle 112 and/or in the inlet tube 1006. In this manner, the coolant may be maintained in a closed loop system and circulated through the ablation probe 110 and the cable 116 to reduce an operating temperature of the probe 110 and/or the cable 116.

Figure 13:
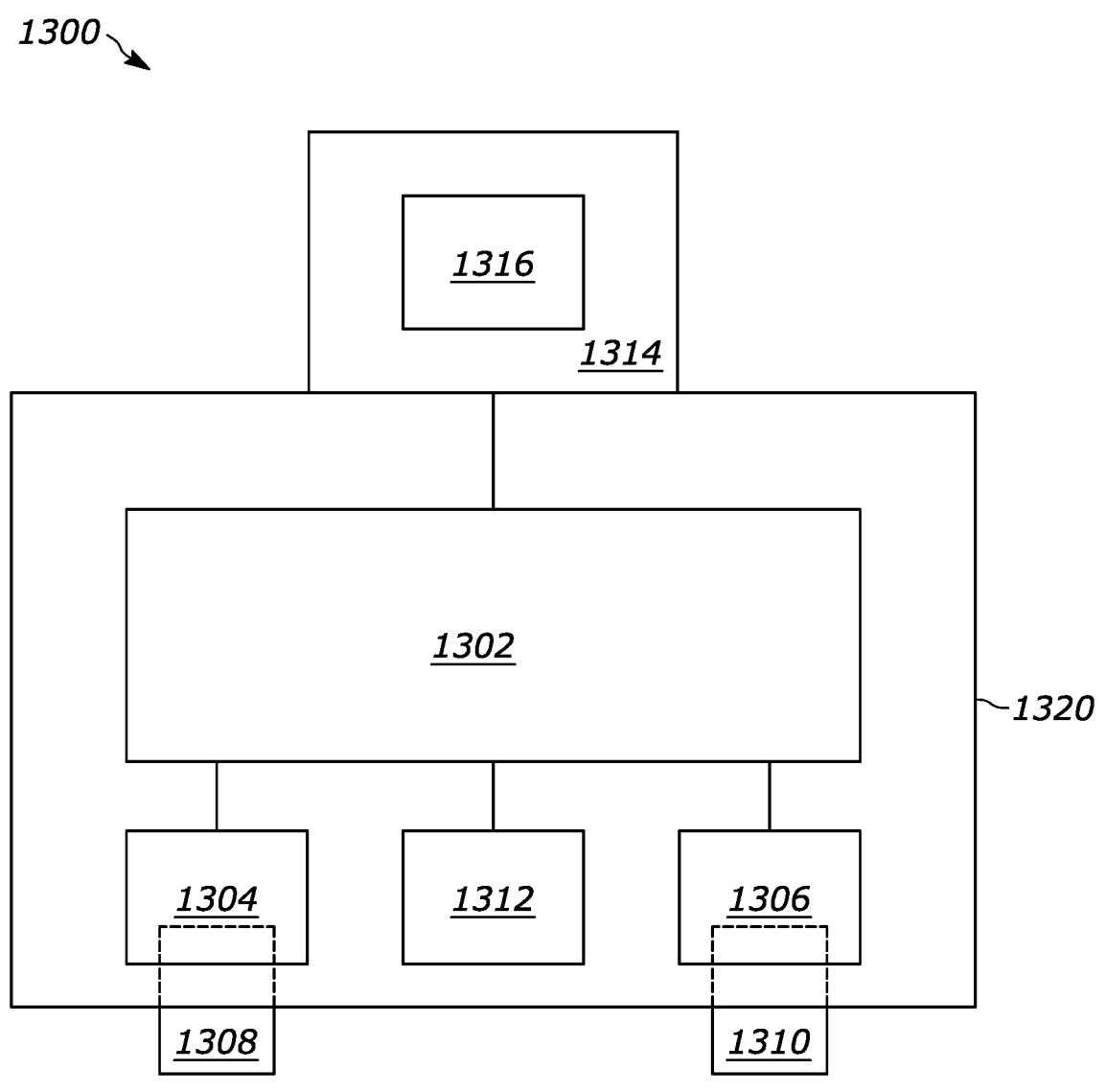
FIG. 13 is a block diagram illustrating an example abla-tion console in accordance with the present disclosure.

The present disclosure also contemplates various methods that may be performed using various embodiments of the cooling systems and ablation consoles of the present disclosure. As previously described, the pump assembly 502 and/or the cassette 114 may be used together as part of an ablation system to perform an ablation treatment. FIG. 13 illustrates an example ablation console 1300 that will be used to describe various methods contemplated in the present disclosure. It should be appreciated, however, that any of the ablation consoles or various elements thereof and variations can be used to perform the methods as well.

As shown, the ablation console 1300 includes a housing 1320 that may enclose a controller 1302, a first pump assembly 1304, a second pump assembly 1306, and a microwave generator 1312. The controller 1302 can be coupled to the first pump assembly 1304, the second pump assembly 1306, and the microwave generator 1312. As such, the controller 1302 can control various aspects and operating conditions of the first pump assembly 1304, the second pump assembly 1306, and the microwave generator 1312. The controller 1302 can be configured as a computing device, PCB, application-specific circuit, programmable logic controller, or other suitable device. The controller 1302 may include, for example, one or more processors, memory, storage mediums, input/output devices, and other elements known to one of ordinary skill in the art. The controller 1302 may also be coupled to a display 1314. The display 1314 may be configured to display a user interface 1316. The display and user interface 1316 may be configured to allow a user to view, choose, select, and input various types of information such as operating parameters of the ablation console 1300.

The console 1300 may also include a first cassette receptacle and a second cassette receptacle. A first cassette 1308 may be received into console 1300 and a second cassette 1310 may be received into the console 1300 as well. The first pump assembly 1304, the second pump assembly 1306, the first cassette 1308, and the second cassette 1310 may be configured as previously described above and/or include variations thereof.

Figure 14:
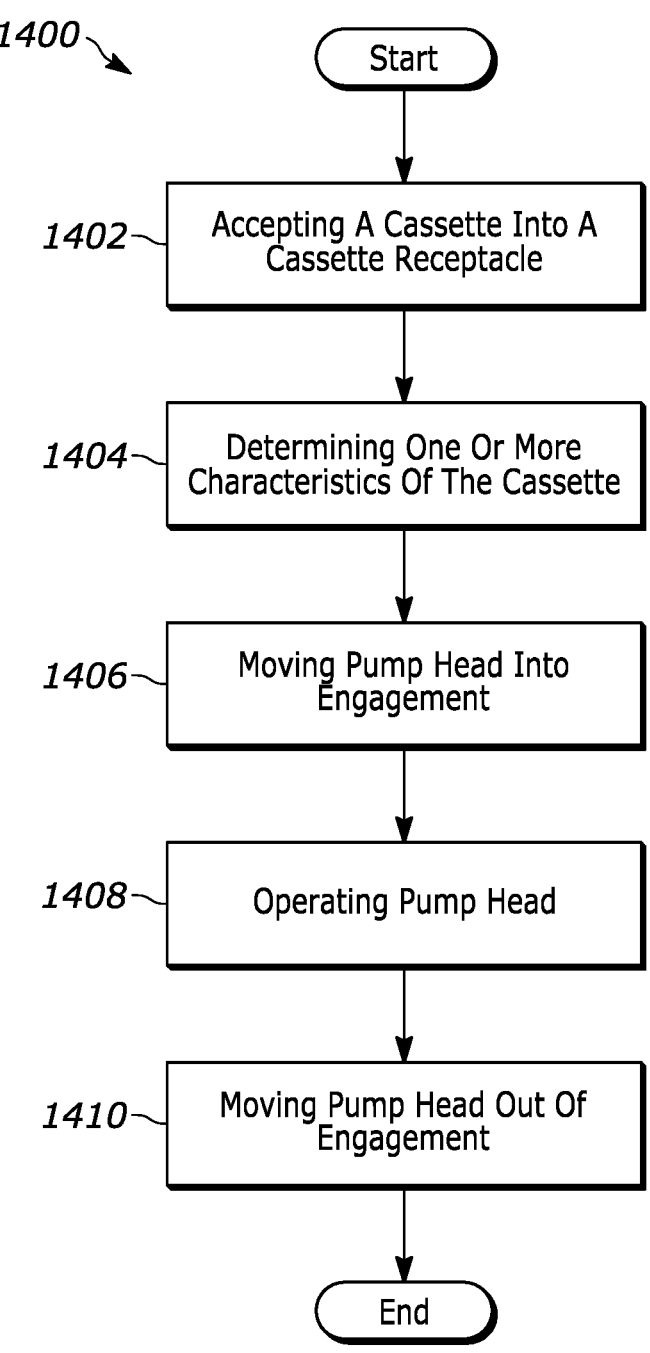
FIG. 14 is a flow chart illustrating an example method of cooling an ablation probe in accordance with the present disclosure.

Turning now to FIG. 14, an example method 1400 is provided. The example method 1400 may be performed, for example, by the console 1300. The method 1400 may begin at step 1402. At step 1402, a cassette 114 may be accepted into a cassette receptacle of the console 1300. The controller 1302 may perform operations at step 1402. The controller 1302 may ensure that the pump head of the pump assemblies 1304, 1306 are in a loading position. The controller 1302 may also display an indicator or icon on user interface 1316 that notifies a user that the console is ready to accept a cassette. A user may then insert the cassette 1308 into the console 1300. As previously described, the user may insert the cassette into the console in an loading direction. In some examples, the loading direction may correspond to a horizontal direction in which the cassette 1308 is inserted into a front face of the console 1300.

The method 1400 may then proceed to step 1404. At step 1404, the controller 1302 may determine one or more characteristics of the cassette 1308. In some examples, the cassette 1308 may include a radio frequency identification (RFID) tag and the console 1300 may include an RFID reading device. The RFID tag may include information regarding a type, size, recommended operating parameters, identification number, patient identifier, or other information. Such information can be obtained by the controller 1302. The controller 1302 may then set, modify, or otherwise determine operating parameters of the console 1300 such as rotational speed of the pump assembly, force to be applied to the supply tube, time, duration, or the like. The controller may automatically send signals to various elements of the console 1300 to prepare the console for an ablation treatment. In other examples, the cassette 1308 may include other features that can indicate such information to the console. The cassette may include, for example, a bar code, quick response (QR) code, pogo-pins, identification number, or the like. An optical sensor, reader or other information collection device in the console 1300 may obtain information from the cassette 1308. In addition, the console 1300 may detect or determine whether the cassette is properly seated and positioned in the console 1300. Magnets, an optical sensor, or other sensor may be used by the controller 1302 to determine if and when the cassette is positioned at a predetermined location in the console 1300.

The method 1400 may then proceed to step 1406. At step 1406, the controller 1302 may send a signal to the actuator of the pump assembly 1304 to cause the pump head of the pump assembly 1304 to move from the loading position to the operating position. In the operating position, the pump head is engaged to the supply tube of the cassette 1308. The controller 1302 may automatically move the pump to the operating position in response to determining that the cassette 1308 is seated and positioned at a predetermined location in the console 1300. The controller 1302 may also receive an input from a user, via the user interface 1316 for example, to indicate that the user desires to move the pump head to the operating position. The controller 1302 may provide an indication of an error or fault if the pump head encounters an obstacle when it is moved to the operating position and/or if the one or more sensors as previously described indicates that the cassette 1308 is not in a proper position in the console 1300.

When the pump head is moved into engagement with the supply tube, the controller 1302 may also cause the pump head to exert a force on the supply tube. The actuator of the pump assembly 1304 may be used for this purpose as previously described. The controller 1302 may set the force exerted by the pump head on the supply to a predetermined force range and/or set one or more predetermined force thresholds. The force ranges and/or force thresholds may be indicated in accordance with the information obtained from the cassette 1308 by the controller 1302.

The controller 1302 may also determine a position of the pump head and/or verify that the pump head is positioned at a predetermined position such as a height above the supply tube and/or above the occlusion plate. Such positioning information of the pump head may be obtained using the position flag and the position sensor as previously described. In other examples, other sensors and positioning indicators may be used by the controller 1302 to determine that the pump head is in a desired position. The controller 1302 may indicate a positioning of the pump head on the user interface 1316.

The method 1400 may then move to step 1408. At step 1408, the controller 1302 may operate the pump head. The controller 1302 may cause, for example, a motor of the pump assembly 1304 to rotate the roller assembly at a predetermined rotational speed. In addition, the roller assembly may exert a predetermined force on the supply tube during such rotation. This action may cause the coolant in the supply tube to flow through the coolant flow path to supply coolant to the ablation probe to remove thermal energy and maintain the ablation probe and/or the cable of the ablation probe assembly below a temperature threshold or within predetermined temperature range. As can be appreciated, the controller 1302 may also cause the microwave generator 1312 to provide a microwave signal to the ablation probe to cause thermal ablation at the target tissue. The controller 1302 may also adjust, modify, and/or maintain a coolant flow in response to receiving temperature or other operating characteristics of the ablation probe assembly. The controller 1302 may operate the pump head for a desired time or in response to input by a user. The ablation treatment and its characteristics such as duration, number of cycles, operating parameters, temperatures and the like may be stored in the memory of the controller 1302, be input by a user, and/or be obtained from a treatment plan.

The method 1400 may then move to step 1410. At step 1410, the controller 1302 may move the pump head out of engagement with the supply tube. At step 1410 (or before), the controller 1302 may have stopped rotation of the roller head assembly. The controller 1302 may raise the pump head or otherwise move the pump head from the operating position to the loading position. This movement may be performed to move the pump head in an engagement direction. The engagement direction, in the example shown, is a vertical direction. The engagement direction may be orthogonal to the loading direction of the cassette 1308 into the console 1300.

Once the pump head is moved out of engagement from the supply tube, the cassette 1308 may be removed from the console 1300. In other instances the method 1400 may end. As can be appreciated, the method 1400 may be repeated if a new or different cassette 1308 is desired to be used to cool an ablation probe. In some instances, the ablation probe assembly may be disposable and a new ablation probe assembly with a new cassette may be used for an ablation treatment. In other circumstances one or more steps may be repeated in the method 1400. For example, if the console 1300 includes more than one cassette receptacle and pump assembly, steps 1402 through 1410 may be repeated for each cassette 1308 that is desired to be used during an ablation treatment. The multiple cassettes may be operated to simultaneously cool multiple ablation probes and cables during some treatments.

The features, structure and related methods of the cooling systems of the present disclosure are improvements over existing or traditional systems and methods. In existing systems, tubing or other elements are loaded into pumping systems manually and the proper engagement and position must be verified by the user. Such existing systems are prone to user error and require significant experience by the user to prevent misalignment, leakage, and proper coolant flow. The systems and methods of the present disclosure allow a cassette to be loaded into the ablation console and the positioning and engagement of the coolant tubing is performed automatically without significant user intervention.

The loading direction of the cassette is a user-friendly direction that differs from existing systems and allows simple set-up and use.

The systems and methods of the present disclosure also provide a pressure-controlled system that alleviates known problems in existing systems such as leakage, inadequate flow, and physical movement of the coolant tubing during operation. The precise control of maximum pressure in the coolant flow path is desirable. Control of the maximum pressure may allow the system to prevent rupture or leakage during operation. The control of the compression force on the supply tubing by the roller assembly in the systems of the present disclosure allow precise, effective, and variable pressure limiting to be achieved. For example, if an occlusion occurs, the maximum created pressure in the tubing is determined by whether the rollers can counteract the pressure that increases in the tubing due to the occlusion. Since the compression force is achieved using a biasing force such a spring in the present system, if the occlusion causes the pressure to increase to a level such that the internal fluid force on the supply tube exceeds the compression force of the roller, the roller will be lifted (forced away from the tube) permitting coolant to backflow under the roller and the roller will not continue to increase pressure in the system. Alternatively, if the pressure in the tubing is not raised to a level that can overcome the compression force of the roller, the roller will continue to compress the tubing and move coolant through the system, preventing backflow and increasing system pressure. Thus, the systems and methods of the present disclosure can be an effective pressure control. Existing systems do not allow for such control of the compression force on the tubing and do not provide this advantage.

The dampening chamber in the cassettes of the present disclosure also are improvements over existing systems. The chambers, as previously described, can trap and hold air as the coolant fills and moves through the coolant flow path. This trapped air in the chamber dampens the pressure oscillations in the system and prevents or reduces undesirable movement of the coolant tubing and ablation probe during operation. The chambers also provide a more consistent, stable flow of coolant than existing systems. Still further, the orientation of the cassettes and the loading direction of the cassettes permits the consoles of the present disclosure to have a more compact size and shape than existing systems.

The example methods and apparatuses described herein may be at least partially embodied in the form of computer-implemented processes and apparatus for practicing those processes and/or the described functionality. The disclosed methods may also be at least partially embodied in the form of tangible, non-transient machine readable storage media encoded with computer program code. The media may include, for example, RAMs, ROMs, CD-ROMs, DVD-ROMs, BD-ROMs, hard disk drives, flash memories, or any other non-transient machine-readable storage medium, or any combination of these mediums, wherein, when the computer program code is loaded into and executed by a computer, the computer becomes an apparatus for practicing the method. The methods may also be at least partially embodied in the form of a computer into which computer program code is loaded and/or executed, such that, the computer becomes an apparatus for practicing the methods. When implemented on a general purpose processor, the computer program code segments configure the processor to create specific logic circuits. The methods may alternatively be at least partially embodied in a digital signal processor formed of application specific integrated circuits for performing the methods.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The following is a list of non-limiting illustrative embodiments disclosed herein:

Illustrative embodiment 1: An apparatus comprising: a cassette receptacle configured to accept a cassette including a supply tube for supplying a coolant to an ablation probe; a pump head movably positioned proximate the cassette receptacle and configured to move between a loading position and an operating position, the pump head comprising one or more rollers configured to engage the supply tube of the cassette when the pump head is in the operating position; and an actuator coupled to the pump head, the actuator configured to move the pump head between the loading position and the operating position.

Illustrative embodiment 2: The apparatus of illustrative embodiment 1, wherein the cassette receptacle is positioned in a front face and configured to accept the cassette in a loading direction.

Illustrative embodiment 3: The apparatus of illustrative embodiment 2, wherein the pump head is configured to move between the loading position and the operating position along an engagement direction, the engagement direction oriented orthogonally to the loading direction.

Illustrative embodiment 4: The apparatus of illustrative embodiment 3, wherein the loading direction is a horizontal direction and the engagement direction is a vertical direction.

Illustrative embodiment 5: The apparatus of any of the preceding illustrative embodiments, wherein: the actuator comprises a spring and a stepper motor; and the spring is configured to apply a predetermined force to the supply tube via the pump head when the stepper motor moves the pump head to the operating position.

Illustrative embodiment 6: The apparatus of illustrative embodiment 5, wherein the predetermined force may be adjusted using the motor to compress the spring to a corresponding predetermined compression value.

Illustrative embodiment 7: The apparatus of any of the preceding illustrative embodiments, wherein the actuator is indirectly coupled to the pump head via one or more arms.

Illustrative embodiment 8: The apparatus of any of the preceding illustrative embodiments, further comprising a first arm and a second arm, the first arm and the second arm each connected to the pump head at a first end and each connected at a rotational axis at a second end, and wherein the actuator is positioned between and coupled to the first arm and the second arm.

Illustrative embodiment 9: The apparatus of any of the preceding illustrative embodiments, further comprising an occlusion plate positioned in the cassette receptacle.

Illustrative embodiment 10: The apparatus of illustrative embodiment 9, wherein the occlusion plate comprises an upward-facing concave shape.

Illustrative embodiment 11: The apparatus of any of illustrative embodiments 9 or 10, wherein the occlusion plate is stationary.

Illustrative embodiment 12: The apparatus of any of the preceding illustrative embodiments, further comprising the cassette.

Illustrative embodiment 13: The apparatus of illustrative embodiment 12, wherein the cassette comprises a case and the case defines an opening, the supply tube extending across the opening.

Illustrative embodiment 14: The apparatus of illustrative embodiment 12, wherein the cassette comprises a chamber positioned inside a case, the chamber fluidly connected to the supply tube, the chamber configured to dampen pressure oscillations during operation of the pump head.

Illustrative embodiment 15: The apparatus of illustrative embodiment 14, wherein an inlet to the chamber is positioned vertically above the outlet of the chamber.

Illustrative embodiment 16: The apparatus of any of illustrative embodiments 12 to 15, wherein the cassette comprises one or more magnets configured to retain the cassette in a desired position in the cassette receptacle.

Illustrative embodiment 17: The apparatus of any of illustrative embodiments 12 to 16, wherein a retainer is coupled to the pump and configured to move with the pump head when the pump head is moved from the loading position to the operating position, the retainer configured to engage and retain the cassette in the cassette receptacle when the pump head is in the operating position.

Illustrative embodiment 18: The apparatus of illustrative embodiment 17, wherein a case of the cassette defines an opening to receive the retainer when the pump head is in the operating position.

Illustrative embodiment 19: The apparatus of any of illustrative embodiments 12 to 18, wherein the supply tube of the cassette is fluidly coupled to a coolant flow path configured to move thermal energy away from a microwave ablation probe.

Illustrative embodiment 20: The apparatus of any of illustrative embodiments 12 to 19, wherein the cassette is part of an ablation probe assembly, the ablation probe assembly comprising a cable and an ablation probe.

Illustrative embodiment 21: The apparatus of any of the preceding illustrative embodiments, further comprising one or more microwave generators configured to deliver a microwave signal to a microwave ablation probe.

Illustrative embodiment 22: A method cooling an ablation probe comprising: accepting a cassette into a cassette receptacle of an ablation console; moving a pump head into engagement with a supply tube of the cassette; and operating the pump head to move coolant through the supply tube.

Illustrative embodiment 23: The method of illustrative embodiment 22, wherein the step of moving the pump into engagement with the supply tube is automatically performed in response to detecting that the cassette is positioned at a predetermined location in the cassette receptacle.

Illustrative embodiment 24: The method of any of illustrative embodiments 22 or 23, wherein the step of moving the pump head comprises applying a predetermined force to the supply tube.

Illustrative embodiment 25: The method of any of illustrative embodiments 22 to 24, further comprising receiving an input from a user of one or more operating parameters, the one or more operating parameters comprising a rotational speed of the pump head and a force to be applied to the supply tube by the pump head.

Illustrative embodiment 26: The method of any of illustrative embodiments 22 to 25, further comprising determining one or more characteristics of the cassette and setting one or more operating parameters based on the one or more characteristics of the cassette.

Illustrative embodiment 27: The method of any of illustrative embodiments 22 to 26, wherein the pump head is moved in an engagement direction that is orthogonal to a loading direction of the cassette into the cassette receptacle.

Illustrative embodiment 28: The method of any of illustrative embodiments 22 to 27, further comprising retaining the cassette in the cassette receptacle when the pump is moved into engagement with the supply tube.

Illustrative embodiment 29: The method of any of illustrative embodiments 22 to 28, further comprising adjusting a force applied by the pump to the supply tube.

Illustrative embodiment 30: The apparatus or ablation console of any of the preceding illustrative embodiments, further comprising at least one cassette sensor positioned proximate the cassette receptacle and configured to determine whether a cassette is present in the cassette receptacle.

Illustrative embodiment 31: The apparatus or ablation console of any of the preceding illustrative embodiments, further comprising a pump head position sensor positioned proximate the pump head and configured to determine a position of the pump head.

Illustrative embodiment 32: The apparatus or ablation console of any of the preceding illustrative embodiments, further comprising a force sensor positioned at or near the pump head and configured to determine a force applied to a supply tube of a cassette.

Illustrative embodiment 33: The apparatus or ablation console of any of the preceding illustrative embodiments, further comprising an actuator position sensor configured to determine a position of a pump assembly or a force applied by the pump assembly.

Illustrative embodiment 34: The apparatus or ablation console of any of the preceding illustrative embodiments, further comprising a reader sensor configured to obtain information regarding a cassette.

What is claimed is:

1. An apparatus comprising:
   a cassette receptacle configured to accept a cassette including a supply tube for supplying a coolant to an ablation probe;
   a pump head movably positioned proximate the cassette receptacle and configured to move between a loading position and an operating position, the pump head comprising one or more rollers configured to engage the supply tube of the cassette when the pump head is in the operating position; and
   an actuator coupled to the pump head, the actuator configured to move the pump head between the loading position and the operating position; and
   a first arm and a second arm each connected to the pump head at a first end and having a common rotational axis at a second end, wherein the actuator is positioned between the common rotational axis and the pump head, and wherein the actuator is configured to move the first arm and the second arm in a first direction and in a second direction opposite the first direction that, in turn, causes movement of the pump head in at least one of the first direction and the second direction.

2. The apparatus of claim 1 comprising a front face, wherein the cassette receptacle is positioned in the front face and configured to accept the cassette in a loading direction.

3. The apparatus of claim 2, wherein the first direction and the second direction are orthogonal to the loading direction.

4. The apparatus of claim 3, wherein the loading direction is a horizontal direction and each of the first direction and the second direction are vertical directions.

5. The apparatus of claim 1, wherein:

the actuator comprises a spring and a stepper motor; and the spring is configured to apply a predetermined force to the supply tube via the pump head when the stepper motor moves the pump head to the operating position.

6. The apparatus of claim 5, wherein the predetermined force may be adjusted using the motor to compress the spring to a corresponding predetermined compression value.

7. The apparatus of claim 1, further comprising an occlusion plate positioned in the cassette receptacle.

8. The apparatus of claim 7, wherein the occlusion plate comprises an upward-facing concave shape.

9. The apparatus of claim 7, wherein the occlusion plate is stationary.

10. The apparatus of claim 1, further comprising the cassette.

11. The apparatus of claim 10, wherein the cassette comprises a case and the case defines an opening, the supply tube extending across the opening.

12. The apparatus of claim 10, wherein the cassette comprises a chamber positioned inside a case, the chamber fluidly connected to the supply tube, the chamber configured to dampen pressure oscillations during operation of the pump head.

13. The apparatus of claim 12, wherein an inlet to the chamber is positioned vertically above an outlet of the chamber.

14. The apparatus of claim 10, wherein the cassette comprises one or more magnets configured to retain the cassette in a desired position in the cassette receptacle.

15. The apparatus of claim 10, wherein a retainer is coupled to the pump head and configured to move with the pump head when the pump head is moved from the loading position to the operating position, the retainer configured to engage and retain the cassette in the cassette receptacle when the pump head is in the operating position.

16. The apparatus of claim 15, wherein a case of the cassette defines an opening to receive the retainer when the pump head is in the operating position.

17. The apparatus of claim 10, wherein the supply tube of the cassette is fluidly coupled to a coolant flow path configured to move thermal energy away from a microwave ablation probe.

18. The apparatus of claim 10 comprising an ablation probe assembly, wherein the cassette is part of the ablation probe assembly, the ablation probe assembly comprising a cable and the ablation probe.

19. The apparatus of claim 1 further comprising one or more microwave generators and a microwave ablation probe, wherein the one or more microwave generators are configured to deliver a microwave signal to the microwave ablation probe.

* * * * *